(12) United States Patent
Aghaei et al.

(10) Patent No.: US 12,424,322 B2
(45) Date of Patent: Sep. 23, 2025

(54) FEDERATED LEARNING SYSTEM FOR TRAINING MACHINE LEARNING ALGORITHMS AND MAINTAINING PATIENT PRIVACY

(71) Applicant: Ventana Medical Systems, Inc., Tucson, AZ (US)

(72) Inventors: Faranak Aghaei, Tucson, AZ (US); Nidhin Murari, Tucson, AZ (US); Jim F. Martin, Tucson, AZ (US); Joachim Schmid, Tucson, AZ (US); Fahime Sheikhzadeh, Tucson, AZ (US); Anirudh Som, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 513 days.

(21) Appl. No.: 17/864,233

(22) Filed: Jul. 13, 2022

(65) Prior Publication Data
US 2022/0351860 A1    Nov. 3, 2022

Related U.S. Application Data

(63) Continuation of application No. PCT/US2021/017491, filed on Feb. 10, 2021.
(Continued)

(51) Int. Cl.
*G16H 50/20* (2018.01)
*G06T 7/00* (2017.01)
*G16H 30/40* (2018.01)

(52) U.S. Cl.
CPC .......... *G16H 50/20* (2018.01); *G06T 7/0012* (2013.01); *G16H 30/40* (2018.01);
(Continued)

(58) Field of Classification Search
CPC ...... G16H 50/20; G16H 30/40; G16H 7/0012; G16H 2207/20021; G16H 2207/20081; G16H 2207/20084; G16H 2207/30024
(Continued)

(56) References Cited

U.S. PATENT DOCUMENTS 7,760,927 B2    7/2010  Gholap et al.
2015/0324686 A1  11/2015  Julian et al.
(Continued)

FOREIGN PATENT DOCUMENTS

JP    2017519282 A    7/2017
JP    2018502275 A    1/2018
(Continued)

OTHER PUBLICATIONS

Application No. PCT/US2021/017491, International Preliminary Report on Patentability, Mailed On Aug. 25, 2022, 9 pages.
(Continued)

*Primary Examiner* — Quang N Vo
(74) *Attorney, Agent, or Firm* — Mughal Gaudry & Franklin PC

(57) ABSTRACT

A method for using a federated learning classifier in digital pathology includes distributing, by a centralized server, a global model to a plurality of client devices. The client devices further train the global model using a plurality images of a specimen and corresponding annotations to generate at least one further trained model. The client devices provide further trained models to the centralized server, which aggregates the further trained models with the global model to generate an updated global model. The updated global model is then distributed to the plurality of client devices.

14 Claims, 9 Drawing Sheets
(3 of 9 Drawing Sheet(s) Filed in Color)

Related U.S. Application Data

(60) Provisional application No. 62/975,036, filed on Feb. 11, 2020.

(52) U.S. Cl.
CPC ............... *G06T 2207/20021* (2013.01); *G06T 2207/20081* (2013.01); *G06T 2207/20084* (2013.01); *G06T 2207/30024* (2013.01)

(58) Field of Classification Search
USPC .......................................................... 382/128
See application file for complete search history.

(56) References Cited

U.S. PATENT DOCUMENTS

| | | | |
|---|---|---|---|
| 2017/0103521 A1* | 4/2017 | Chukka | G06V 20/695 |
| 2017/0140246 A1 | 5/2017 | Barnes et al. | |
| 2019/0042937 A1 | 2/2019 | Sheller et al. | |
| 2020/0293887 A1* | 9/2020 | De Brouwer | G06N 3/084 |

FOREIGN PATENT DOCUMENTS

| | | |
|---|---|---|
| WO | 2014102130 A1 | 7/2014 |
| WO | 2014140085 A1 | 9/2014 |
| WO | 2015049233 A1 | 4/2015 |
| WO | 2015181371 A1 | 12/2015 |
| WO | 2016061586 A1 | 4/2016 |
| WO | 2016120442 A1 | 8/2016 |
| WO | 2018098039 A1 | 5/2018 |
| WO | 2019110567 A1 | 6/2019 |
| WO | 2019178561 A2 | 9/2019 |
| WO | 2019216938 A1 | 11/2019 |

OTHER PUBLICATIONS

Application No. PCT/US2021/017491, International Search Report and Written Opinion, Mailed On May 31, 2021, 13 pages.

Barton, et al., "Assessment of the Contribution of the IHC4+C Score to Decision Making in Clinical Practice in Early Breast Cancer", British Journal of Cancer, 2012, 106(11), pp. 1760-1765.

Cuzick, et al., "Prognostic Value of a Combined Estrogen Receptor, Progesterone Receptor, Ki-67, and Human Epidermal Growth Factor Receptor 2 Immunohistochemical Score and Comparison with the Genomic Health Recurrence Score in Early Breast Cancer", Journal of Clinical Oncology, vol. 29, No. 32, 2011, pp. 4273-4278.

Li, et al., "Privacy-Preserving Federated Brain Tumour Segmentation", Oct. 2019, MICCAI MLMI, 8 pages.

Parvin, et al., "Iterative Voting for Inference of Structural Saliency and Characterization of Subcellular Events", Image Processing, IEEE Transactions on 16.3 (2007): 615-623.

Verma, et al., "Approaches to address the data skew problem in federated learning", Proceedings of the SPIE, vol. 11006, 2019, 16 pages.

Communication pursuant to Article 94(3) for European Patent Application No. 21710684.8, dated Jul. 4, 2024.

Notice of Reasons for Rejection for Japanese patent application No. 2022-547853, dated Jan. 14, 2025.

\* cited by examiner

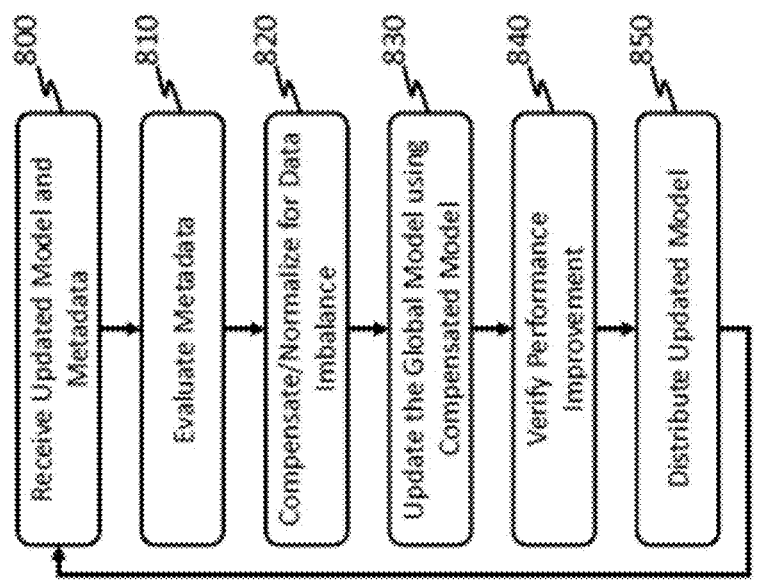

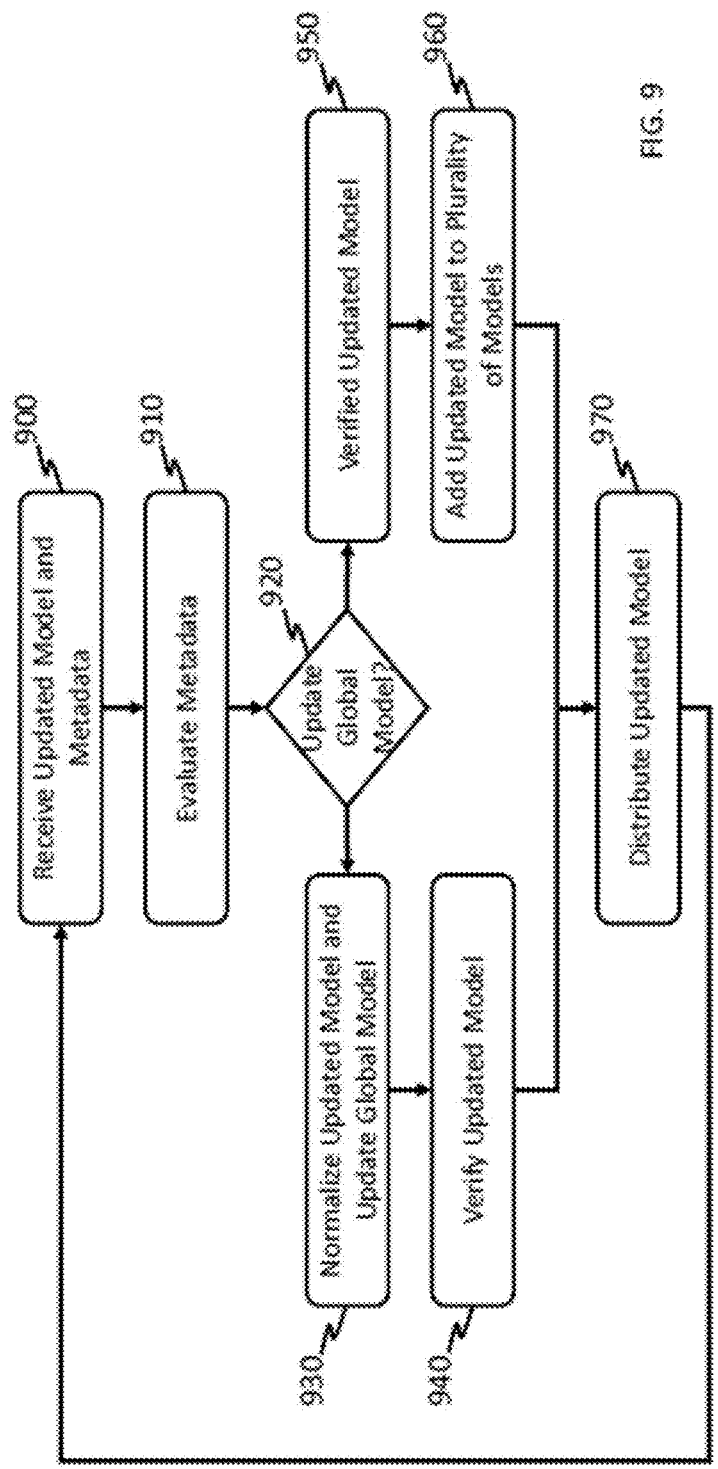

FEDERATED LEARNING SYSTEM FOR TRAINING MACHINE LEARNING ALGORITHMS AND MAINTAINING PATIENT PRIVACY

CROSS-REFERENCE

The present application is a continuation, which claims priority and benefit from International Application PCT/US2021/017491, filed Feb. 10, 2021, which claims priority and benefit from U.S. Provisional Application No. 62/975,036, filed Feb. 11, 2020, the entire contents of which are incorporated herein by reference for all purposes.

FIELD

The present disclosure relates to digital pathology, and in particular to machine learning techniques for federated learning.

BACKGROUND

Digital pathology involves scanning of pathology slides having tissue and/or cells (e.g., histopathology or cytopathology glass slides) into digital images for use in evaluation. The tissue and/or cells within the digital images may be subsequently examined using digital pathology image analysis and/or interpreted by a pathologist for a variety of reasons including diagnosis of disease, assessment of a response to therapy, and the development of pharmalogical agents to fight disease. In order to examine the tissue and/or cells within the digital images (which are virtually transparent), the pathology slides may be prepared using colored stains (e.g., immunostains) that bind selectively to tissue and/or cellular components. Immunohistochemistry (IHC) is a common application of immunostaining and involves the process of selectively identifying antigens (proteins) in cells of a tissue section by exploiting the principle of antibodies and other compounds (or substances) binding specifically to antigens in biological tissues. In some assays, the target antigen in the specimen to a stain may be referred to as a biomarker. Thereafter, digital pathology image analysis can be performed on digital images of the stained tissue and/or cells to identify and quantify staining for antigens (e.g., biomarkers indicative of tumor cells) in biological tissues.

Machine learning techniques have shown great promise in digital pathology image analysis, such as in tumor region identification, metastasis detection, and patient prognosis. Many computing systems provisioned with machine learning techniques, including convolutional neural networks (CNNs), have been proposed for image classification and digital pathology image analysis, such as tumor region and metastasis detection. For example, CNNs can have a series of convolution layers as the hidden layers and this network structure enables the extraction of representational features for object/image classification and digital pathology image analysis. In addition to object/image classification, machine learning techniques have also been implemented for image segmentation. Image segmentation is the process of partitioning a digital image into multiple segments (sets of pixels, also known as image objects). The typical goal of segmentation is to simplify and/or change the representation of an image into something that is more meaningful and easier to analyze. For example, image segmentation is often used to locate objects such as tumors (or other tissue types) and boundaries (lines, curves, etc.) in images. To perform image segmentation for large data (e.g., whole slide pathology images), the image is first divided into many small patches. A computing system provisioned with machine learning techniques is trained to classify these patches, and all patches in a same class are combined into one segmented area. Thereafter, machine learning techniques may be further implemented to predict or classify the segmented area (e.g., negative tumor cells or tumor cells that have no stain expression) based on representational features associated with the segmented area.

Various machine learning techniques require training data in order to establish a ground truth for performing classification. In the medical field, patient data is often difficult to obtain due to privacy concerns and legal requirements. Thus, properly training a classifier can pose a challenge. Federated learning is a decentralized machine learning technique that involves providing base classifier to one or more client devices. Each of the devices may then operate using the base classifier. As the classifier is utilized on each of the devices, users provide input regarding the outputs provided by the classifiers. Users may provide input to their respective classifier based on the outputs and each of the respective classifiers may be updated according to the user inputs. The updated classifiers may then be provided to update the base classifier. The updated classifier may then be distributed to the client devices. Thus, a federated learning system is capable of updating without the need to pass data between entities.

SUMMARY

In various embodiments, a computer-implemented method is provided.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

Some embodiments of the present disclosure include a computer-implement method for using a federated learning classifier. The method includes distributing, by a centralized server, a global model configured to classify pathology images to a plurality of client devices; receiving, by the centralized server an updated model from at least one of the plurality of client devices, wherein the updated model has been further trained at the at least one of the plurality of client devices using a plurality of slide images and a plurality of corresponding annotations; aggregating, by the centralized server, the updated model with the global model to generate an updated global model; and distributing the updated global model to at least one of the plurality of client devices.

Some embodiments of the present disclosure include a computer-implemented method where aggregating the updated model with the global model to generate an updated global model includes performing an averaging of a least one weight of the global model with at least on weight of the updated model.

Some embodiments of the present disclosure include a computer-implemented method, wherein performing the averaging comprises performing a weighted average according of the at least one weight of the updated model with the at least one weight of the global model according to number of the plurality of slide images used to further train the updated model and a total number of images used to train the global model.

Some embodiments of the present disclosure include a computer-implemented method wherein the annotations are provided by a user observing an output of the global model on a slide image and the annotations comprise a modification to the output produced by the global model.

Some embodiments of the present disclosure include a computer-implemented method that further includes receiving, by the centralized server, metadata associated with the plurality of slide images, wherein aggregating further inclues normalizing the further trained model according to the metadata.

Some embodiments of the present disclosure include a computer-implemented method further includes verifying, by the centralized server, a performance improvement of the updated global model relative to the global model using a validation dataset.

Some embodiments of the present disclosure include a computer-implement method for using a federated learning classifier by a client device. The method includes receiving a global model configured to classify pathology images from a centralized server; receiving a stained tissue image, wherein the stained tissue image is divided into image patches; performing an image analysis using the global model on the image patches; training the global model using image patches and at least one corresponding user annotation to generate an updated model, wherein the at least one corresponding user annotation comprises a correction of a classification produced by the global model; sending the updated model to the centralized server; receiving an updated global model; verifying a performance improvement of the updated global using a client specific validation dataset.

Some embodiments of the present disclosure include a computer-implemented method wherein the correction of the classification produced by the global model is a reclassification of at least one of a cell type, a tissue type, or a tissue boundary.

Some embodiments of the present disclosure include a computer-implemented method wherein the updated model contains no individual patient information.

Some embodiments of the present disclosure include a computer-implemented method further including generating metadata relevant to the plurality of images and providing the metadata to the centralized server.

Some embodiments of the present disclosure include a computer-implemented method wherein the metadata comprises at least one of a region of a slide or tissue that the image corresponds, a type of staining performed, a concentrations of a stain, and an equipment used in staining or scanning.

Some embodiments of the present disclosure include a computer-implemented method wherein sending the updated model is performed after a threshold a number of iterations, length of time, or after the model has been modified more than a threshold amount.

Some embodiments of the present disclosure include a computer-implement method for using a federated learning classifier in digital pathology. The method includes distributing, by a centralized server, a global model to a plurality of client devices; training, by a client device from the plurality of client devices, the global model using a plurality images of a specimen to generate at least one further trained model, wherein one or more images of the plurality images comprise at least one annotation; providing, by the client device, the further trained model, to the centralized server; aggregating, by the centralized server, the further trained model with the global model to generate an updated global model; and distributing the updated global model to the plurality of client devices.

Some embodiments of the present disclosure include a computer-implemented method further performing generating, by the client device, metadata relevant to the plurality of images; and providing, by the client device, the metadata to the centralized server, wherein aggregating, by the centralized server, the further trained model with the global model to generate an updated global model further comprises normalizing the further trained model according to the metadata.

Some embodiments of the present disclosure include a computer-implemented method wherein the metadata comprises at least one of a region of a slide or tissue that the image corresponds, a type of staining performed, a concentrations of a stain, and an equipment used in staining or scanning.

Some embodiments of the present disclosure include a computer-implemented method further configured to verify, by the centralized server, a performance of the updated global model relative to the global model using a validation dataset.

Some embodiments of the present disclosure include a computer-implemented method further configured to roll back the update to the global model when the performance of the updated global model is inferior to the global model.

Some embodiments of the present disclosure include computer-implemented method of wherein aggregating the updated model with the global model to generate an updated global model comprises performing an averaging of a least one weight of the global model with at least on weight of the updated model.

Some embodiments of the present disclosure include a computer-implemented method wherein performing the averaging comprises performing a weighted average according of the at least one weight of the updated model with the at least one weight of the global model according to number of the plurality of slide images used to further train the updated model and a total number of images used to train the global model.

Some embodiments of the present disclosure include a computer-implemented method wherein sending the updated model is performed after a threshold a number of iterations, length of time, or after the model has been modified more than a threshold amount.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure is described in conjunction with the appended figures:

FIG. 8 shows a process for a round of FL training of prediction models in accordance with various embodiments;

FIG. 9 shows a process for a receiving an updated model from a client in accordance with various embodiments;

Figure 1:
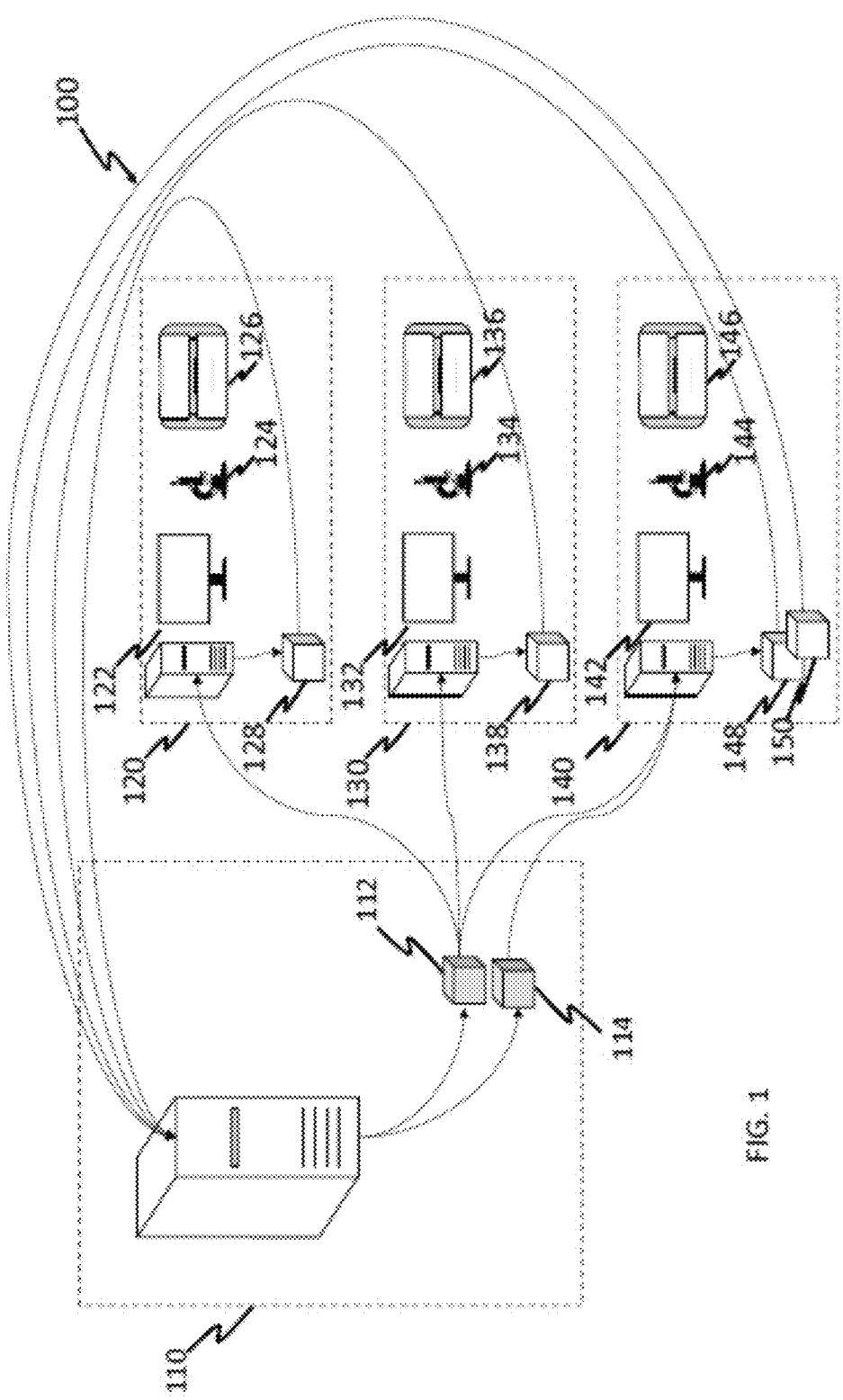
FIG. 1 shows an example a federated learning digital pathology system according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The present disclosure describes techniques for a Digital Pathology (DP) Federated Learning (FL) system. FL is a distributed machine learning approach in which multiple client devices are used collaboratively to train a deep learning model (global model) for performing image analysis without sharing training data. A server is configured to distribute a global model to one or more clients. The server is configured to maintain, update, and redistribute the global model as part of an iterative process. At each iteration (or round), each client may receive the global model to perform DP image analysis on local data (e.g., patient data including pathology slides). The clients may utilize their locally available data (e.g., the patient data and user input) to further train the global model. An updated model may periodically be sent from one or more clients to the server. The updated models may be incorporated into the global model to produce an updated global model. The updated global model may then be distributed to the clients. The iterations continue indefinitely or, for example, until the training converges. In some examples, the received updated models may not be integrated into the global model.

Immunohistochemical (IHC) slide staining can be utilized to identify proteins in cells of a tissue section and hence is widely used in the study of different types of cells, such as cancerous cells and immune cells in biological tissue. It is possible to assess the IHC stained cells of a tissue section under a microscope at high magnification and/or to automatically analyze digital images of the biological specimen with a digital pathology algorithm. Often, in whole slide analysis, the assessment of the stained biological specimen requires segmentation of regions of the stained biological specimen including identification of target regions (e.g., positive and negative tumor cells) and the exclusion of non-target regions (e.g., normal tissue or blank slide regions). In some instances, the non-target regions to be excluded comprise biological material or structures that can be very difficult to differentiate from other biological material or structures of target regions, and thus exclude from the assessment of the biological specimen. As a result, in such instances a pathologist typically provides manual tumor annotations while excluding non-target regions. However, manual tumor annotations are subject to error, pathologist bias, and laborious due to large size of the whole slide images at high magnification and the large volume of data to be processed.

Automated segmentation and classification of tumors and tumor cells can be difficult for a variety of reasons. For example, tumors and tumor cells may vary largely across patients in terms of size, shape, and localization. This prohibits the use of strong priors on shape and localization that are commonly used for robust image analysis in many other applications, such as facial recognition or navigation. As a result, conventional image analysis algorithms usually provide undesired detection results (e.g., over-detection or miss-classification) of these difficult regions.

In order to address these limitations and problems, a large variety and quantity of training data is needed. Given the privacy concerns related to medical data, obtaining large quantities of training data has proven to be difficult. The techniques for FL DP system of the present embodiments include the use of a machine learning architecture that allows for the use of data at client locations for training without the need to send the data to a centralized location. Thus, a patient's private information does not leave its original location and privacy concerns are alleviated. One illustrative embodiment of the present disclosure is directed to a computer-implemented method for automatically performing image analysis on pathology slides, including performing pre-processing, image analysis, and post-processing. For example, the FL DP system may include one or more deep learning architectures that utilize FL to improve performance while not transferring underlying training data between entities. For example, the FL DP system may include a deep learning preprocessing system (e.g., for performing segmentation of an image to remove or mask certain areas), a deep learning system for image processing (e.g., to identify areas of an image having desired features), and/or a deep learning system for performing post-processing (e.g., utilizing the identified areas of an image to perform further analysis). Thus, the FL DP system may include multiple models at each client device and each model may utilize FL.

In some embodiments, the computer-implemented method may include the use of one or more models. The models may have a convolutional neural network (CNN) architecture or model that, for example, utilizes a two-dimensional segmentation model (e.g., a modified U-Net or other suitable architecture) to automatically detect and exclude biological structures or non-tumor cells before performing a standard image analysis algorithm to learn and recognize target regions. Post-analysis may then be performed in order to provide or aid in the provision of a diagnosis or further course of action. The convolutional neural network architecture or model may be trained using pre-labeled images. Consequently, a model (e.g., a trained convolutional neural network architecture or model) may be used to segment the non-target regions, which can then be masked out from the whole slide analysis before, during, or after inputting images to an image analysis algorithm. The image analysis model (e.g., a CNN) performs classification tasks and outputs tumor readouts for the target regions. The post-processing model performs further classification based upon the tumor readouts. Advantageously, this proposed architecture and techniques can improve accuracy of tumor cell classification by improving the models used at every stage of the analysis of the image.

As used herein, when an action is "based on" something, this means the action is based at least in part on at least a part of the something.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As used herein, the term "sample" "biological sample" or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "biological material or structure" refers to natural materials or structures that comprise a whole or a part of a living structure (e.g., a cell nucleus, a cell membrane, cytoplasm, a chromosome, DNA, a cell, a cluster of cells, or the like).

As used herein, the term "non-target region" refers to a region of an image having image data that is not intended to be assessed in an image analysis process. Non-target regions may include non-tissue regions of an image corresponding to a substrate such as glass with no sample, for example where there exists only white light from the imaging source. Non-target regions may additionally or alternatively include tissue regions of an image corresponding to biological material or structures that are not intended to be analyzed in the image analysis process or difficult to differentiate from biological material or structures within target regions (e.g., lymphoid aggregates).

As used herein, the term "target region" refers to a region of an image including image data that is intended be assessed in an image analysis process. Target regions include any region such as tissue regions of an image that is intended to be analyzed in the image analysis process.

As used herein, the term "tile" or "tile image" refers to a single image corresponding to a portion of a whole image, or a whole slide. In some embodiments, "tile" or "tile image" refers to a region of a whole slide scan or an area of interest having (x,y) pixel dimensions (e.g., 1000 pixels by 1000 pixels). For example, consider a whole image split into M columns of tiles and N rows of tiles, where each tile within the M×N mosaic comprises a portion of the whole image, i.e. a tile at location MI,NI comprises a first portion of an image, while a tile at location M3,N4 comprises a second portion of the image, the first and second portions being different. In some embodiments, the tiles may each have the same dimensions (pixel size by pixel size).

As used herein, the term "patch" or "image patch" refers to a container of pixels corresponding to a portion of a tile image, a whole image, or a whole slide. In some embodiments, "patch" or "image patch" refers to a region of a tile image or an area of interest having (x,y) pixel dimensions (e.g., 256 pixels by 256 pixels). For example, a tile image of 1000 pixels by 1000 pixels divided into 100 pixel×100 pixel patches would comprise 100 patches (each patch containing 1000 pixels). In other examples, the patches may overlap.

In some embodiments, a Federated Learning (FL) system for Digital Pathology (DP) may be utilized to generate and distribute a global model (e.g., an aggregated global model) without exchanging sensitive or identifying data (e.g., patient data) between clients and/or a centralized system (e.g., a server). A server is configured to maintain and distribute the global model in an iterative process as updated models are received from clients. FIG. 1 depicts an example a FL DP system 100 that includes one or more servers 110 configured to maintain and distribute one or more global models 112, 114. The server 110 is in communication with one or more client systems 120, 130, 140 that may each include various DP equipment such as a workstation 122, 132, 142, a microscope 124, 134, 144, a digital slide scanner 126, 136, 146, and any other necessary equipment as would be understood by those skilled in the art. Each of the client systems may utilize one or more local models 128, 138, 148, 150 that are based on the global models 112, 114. The client systems 120, 130, 140 may be utilized to further train the local models 128, 138, 148, 150. For example, the client systems 120, 130, 140 may receive patient data, classify the patient data using the local models 128, 138, 148, 150, receive user input regarding the classified patient data (e.g., from a pathologist or other medical professional utilizing a graphical user interface displaying the classified data), and update the local model 128, 138, 148, 150 based on the user input (e.g., each client retrains the global model by using a local training dataset). In various embodiments, the client devices are configured to periodically provide their local models 128, 138, 148, 150 to the centralized server 110. The centralized server 110 may then utilize the local models 128, 138, 148, 150 to update the global model 112, 114 (e.g., by updating weights in the global model) and distribute the updated global model 112, 114 to the client systems 120, 130, 140.

In some embodiments, after each iteration, the performance each of the updated local models 128, 138, 148, 150 may be ascertained using a validation dataset. When a local model 128, 138, 148, 150 has been determined to provide improved performance on the validation dataset, the local model may be incorporated into the global model 112, 114. The performance of the updated global model 112, 114 may also be validated with a validation dataset. If the global model 112, 114 has been improved, the updated global model 112, 114 may be distributed to all or some of the client devices 120, 130, 140. In some embodiments, a client may elect to not share their updated local model 128, 138, 148, 150, but still receive the updated global model 112, 114. In other embodiments, a client may elect to share their local model 128, 138, 148, 150, but not receive any updated global models 112, 114. In other embodiments, a client may elect to not share their updated local model 128, 138, 148, 150 and not receive the updated global model 112, 114. Thus, models that are generated at the client site are not controlled by the centralized server 110 and are shared with the centralized server 110 based on the client's discretion. Each client may have an independent validation dataset and may use the validation dataset to examine the performance of the model based on their quality standards. Based on this validation, the client may determine whether to deploy the global model 112, 114 or not.

In some embodiments, after each iteration, the performance each of the updated local models 128, 138, 148, 150 may be ascertained using a validation dataset. When a local model 128, 138, 148, 150 has been determined to provide improved performance on the validation dataset, the local model may be incorporated into the global model 112, 114. The performance of the updated global model 112, 114 may also be validated with a validation dataset. If the global model 112, 114 has been improved, the updated global model 112, 114 may be distributed to all or some of the client devices 120, 130, 140. In some embodiments, a client may elect to not share their updated local model 128, 138, 148, 150, but still receive the updated global model 112, 114. In other embodiments, a client may elect to share their local model 128, 138, 148, 150, but not receive any updated global models 112, 114. In other embodiments, a client may elect to not share their updated local model 128, 138, 148, 150 and not receive the updated global model 112, 114. Thus, models that are generated at the client site are not controlled by the centralized server 110 and are shared with the centralized server 110 based on the client's discretion. Each client may have an independent validation dataset and may use the validation dataset to examine the performance of the model based on their quality standards. Based on this validation, the client may determine whether to deploy the updated global model 112, 114 or not.

Figure 2:
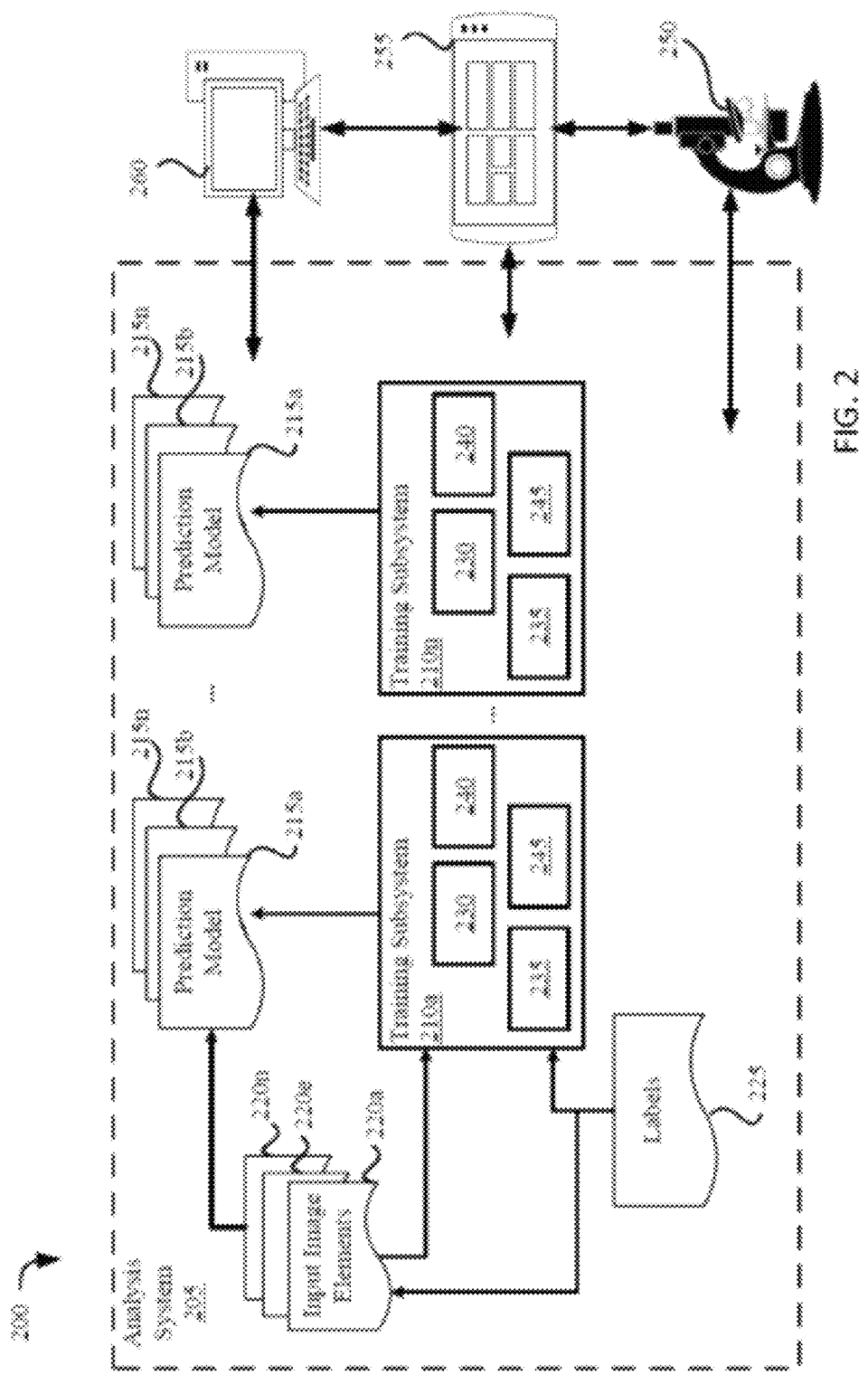
FIG. 2 shows a block diagram illustrating a computing environment for non-tumor segmentation and image analysis using deep convolutional neural networks according to various embodiments.

FIG. 2 shows a block diagram illustrates a computing environment 200 for non-tumor segmentation and image analysis using deep convolutional neural networks according to various embodiments. The computing environment 200 can include an analysis system 205 to train and execute prediction models, e.g., two-dimensional CNN models. More specifically, the analysis system 205 can include training subsystems 210a-n ('a' and 'n' represents any natural number) that build and train their respective prediction models 215a-n (which may be referred to herein individually as a prediction model 215 or collectively as the prediction models 215) to be used by other components of the environment computing 200. A prediction model 215 can be a machine-learning ("ML") or deep-learning ("DL") model, such as a deep convolutional neural network (CNN), e.g. a U-Net neural network, an inception neural network, a residual neural network ("Resnet"), or a recurrent neural network, e.g., long short-term memory ("LSTM") models or gated recurrent units ("GRUs") models. A prediction model 215 can also be any other suitable ML model trained to segment non-target regions (e.g., lymphoid aggregate regions), segment target regions, or provide image analysis of target regions, such as a two-dimensional CNN ("2DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). The computing environment 200 may employ the same type of prediction model or different types of prediction models trained to segment non-target regions, segment target regions, or provide image analysis of target regions. For example, computing environment 200 can include a first prediction model (e.g., a U-Net) for segmenting non-target regions (e.g., lymphoid aggregate regions, necrotic regions, or any other suitable regions). The computing environment 200 can also include a second prediction model (e.g., a 2DCNN) for segmenting target regions (e.g., regions of tumor cells). The computing environment 200 can also include a third model (e.g., a CNN) for image analysis of target regions. The computing environment 200 can also include a fourth model (e.g., a HMM) for diagnosis of disease for treatment or a prognosis for a subject such as a patient. Still other types of prediction models may be implemented in other examples according to this disclosure. Furthermore, multiple models may be used to classify different cell types and regions.

In various embodiments, each prediction model 215a-n corresponding to the classifier subsystems 210a-n may be based on a global model 112, 114 provided by the server 110. In various embodiments, each prediction model 215a-n corresponding to the classifier subsystems 210a-n is separately additionally trained based on one or more sets of input image elements 220a-n. In some embodiments, each of the input image elements 220a-n include image data from one or more scanned slides. Each of the input image elements 220a-n may correspond to image data from a single specimen and/or a single day on which the underlying image data corresponding to the image was collected. The image data may include an image, as well as any information related to an imaging platform on which the image was generated. For instance, a tissue section may need to be stained by means of application of a staining assay containing one or more different biomarkers associated with chromogenic stains for brightfield imaging or fluorophores for fluorescence imaging. Staining assays can use chromogenic stains for brightfield imaging, organic fluorophores, quantum dots, or organic fluorophores together with quantum dots for fluorescence imaging, or any other combination of stains, biomarkers, and viewing or imaging devices. Moreover, a typical tissue section is processed in an automated staining/assay platform that applies a staining assay to the tissue section, resulting in a stained sample. There are a variety of commercial products on the market suitable for use as the staining/assay platform, one example being the VENTANA SYMPHONY product of the assignee Ventana Medical Systems, Inc. Stained tissue sections may be supplied to an imaging system, for example on a microscope or a whole-slide scanner having a microscope and/or imaging components, one example being the VENTANA iScan Coreo product of the assignee Ventana Medical Systems, Inc. Multiplex tissue slides may be scanned on an equivalent multiplexed slide scanner system. Additional information provided by the imaging system may include any information related to the staining platform, including a concentration of chemicals used in staining, a reaction times for chemicals applied to the tissue in staining, and/or pre-analytic conditions of the tissue, such as a tissue age, a fixation method, a duration, how the section was embedded, cut, etc.

The input image elements 220a-n may include one or more training input image elements 220a-d, validation input image elements 220e-g, and unlabeled input image elements 220h-n. It should be appreciated that input image elements 220a-n corresponding to the training, validation and unlabeled groups need not be accessed at a same time. For example, set of training and validation input image elements 220a-n may first be accessed and used to further train a prediction model 215, and unlabeled input image elements may be subsequently accessed or received (e.g., at a single or multiple subsequent times) and used to by the further trained prediction model 215 to provide desired output (e.g., segmentation of non-target regions). In some instances, the prediction models 215a-n are trained using supervised training, and each of the training input image elements 220a-d and optionally the validation input image elements 220e-g are associated with one or more labels 225 that identify a "correct" interpretation of non-target regions, target regions, and identification of various biological material and structures within training input image elements 220a-d and the validation input image elements 220e-g. Labels may alternatively or additionally be used to classify a corresponding training input image elements 220a-d and the validation input image elements 220e-g, or pixel therein, with regards to a presence and/or interpretation of a stain associated with a normal or abnormal biological structure (e.g., a tumor cell). In certain instances, labels may alternatively or additionally be used to classify a corresponding training input image elements 220a-d and the validation input image elements 220e-g at a time point corresponding to when the underlying image was/were taken or a subsequent time point (e.g., that is a predefined duration following a time when the image(s) was/were taken).

In some embodiments, the classifier subsystems 210a-n include a feature extractor 230, a parameter data store 235, a classifier 240, and a trainer 245, which are collectively used to train the prediction models 215 based on training data (e.g., the training input image elements 220a-d) and optimizing the parameters of the prediction models 215 during supervised or unsupervised training. In some instances, the training process includes iterative operations to find a set of parameters for the prediction model 215 that minimizes a loss function for the prediction models 215. Each iteration can involve finding a set of parameters for the prediction model 215 so that the value of the loss function using the set of parameters is smaller than the value of the loss function using another set of parameters in a previous iteration. The loss function can be constructed to measure the difference between the outputs predicted using the prediction models 215 and the labels 225 contained in the training data. Once the set of parameters are identified, the prediction model 215 has been trained and can be utilized for segmentation and/or prediction as designed.

In some embodiments, the classifier subsystem 210a-n accesses training data from the training input image elements 220a-d at the input layers. The feature extractor 230 may pre-process the training data to extract relevant features (e.g., edges, colors, textures, or any other suitable relevant features) detected at particular parts of the training input image elements 220a-d. The classifier 240 can receive the extracted features and transform the features, in accordance with weights associated with a set of hidden layers in one or more prediction models 215, into one or more output metrics that segment non-target or target regions, provide image analysis, provide a diagnosis of disease for treatment or a prognosis for a subject such as a patient, or a combination thereof. The trainer 245 may use training data corresponding to the training input image elements 220a-d to train the feature extractor 230 and/or the classifier 240 by facilitating learning of one or more parameters. For example, the trainer 245 can use a backpropagation technique to facilitate learning of weights associated with a set of hidden layers of the prediction model 215 used by the classifier 240. The backpropagation may use, for example, a stochastic gradient descend (SGD) algorithm to cumulatively update the parameters of the hidden layers. Learned parameters may include, for instance, weights, biases, and/or other hidden layer-related parameters, which can be stored in the parameter data store 235.

Individually or an ensemble of trained prediction models can be deployed to process unlabeled input image elements 220h-n to segment non-target or target regions, provide image analysis, provide a diagnosis of disease for treatment or a prognosis for a subject such as a patient, or a combination thereof. More specifically, a trained version of the feature extractor 230 may generate a feature representation of an unlabeled input image element, which can then be processed by a trained version of the classifier 240. In some embodiments, image features can be extracted from the unlabeled input image elements 220h-n based on one or more convolutional blocks, convolutional layers, residual blocks, or pyramidal layers that leverage dilation of the prediction models 215 in the classifier subsystems 210a-n. The features can be organized in a feature representation, such as a feature vector of the image. The prediction models 215 can be trained to learn the feature types based on classification and subsequent adjustment of parameters in the hidden layers, including a fully connected layer of the prediction models 215.

In some embodiments, the image features extracted by the convolutional blocks, convolutional layers, residual blocks, or pyramidal layers include feature maps that are matrix of values that represent one or more portions of the specimen slide at which one or more image processing operations have been performed (e.g., edge detection, sharpen image resolution). These feature maps may be flattened for processing by a fully connected layer of the prediction models 215, which outputs a non-target region mask, target region mask, or one or more metrics corresponding to a present or future prediction pertaining to a specimen slide. For example, an input image element can be fed to an input layer of a prediction model 215. The input layer can include nodes that correspond with specific pixels. A first hidden layer can include a set of hidden nodes, each of which is connected to multiple input-layer nodes. Nodes in subsequent hidden layers can similarly be configured to receive information corresponding to multiple pixels. Thus, hidden layers can be configured to learn to detect features extending across multiple pixels. Each of one or more hidden layers can include a convolutional block, convolutional layer, residual block, or pyramidal layer. The prediction model 215 can further include one or more fully connected layers (e.g., a softmax layer).

At least part of the training input image elements 220a-d, the validation input image elements 220e-g and/or the unlabeled input image elements 220h-n may include or may have been derived from data obtained directly or indirectly from a source that may be but need not be an element of the analysis system 205. In some embodiments, the computing environment 200 comprises an imaging device 250 that images a sample to obtain the image data, such as a multi-channel image (e.g., a multi-channel fluorescent or brightfield image) with several (such as between ten to sixteen for example) channels. The image device 250 may include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. An image sensor, for example, a CCD sensor can capture a digital image of the specimen. In some embodiments, the imaging device 250 is a brightfield imaging system, a multi spectral imaging (MSI) system or a fluorescence microscopy system. The imaging device 250 may utilize nonvisible electromagnetic radiation (UV light, for example) or other imaging techniques to capture the image. For example, the imaging device 250 may comprise a microscope and a camera arranged to capture images magnified by the microscope. The image data received by the image analysis system 205 may be identical to and/or derived from raw image data captured by the imaging device 250.

In some instances, labels 225 associated with the training input image elements 220a-d and/or validation input image elements 220e-g may have been received or may be derived from data received from one or more provider systems 255, each of which may be associated with (for example) a physician, nurse, hospital, pharmacist, etc. associated with a particular subject. The received data may include (for example) one or more medical records corresponding to the particular subject. The medical records may indicate (for example) a professional's diagnosis or characterization that indicates, with respect to a time period corresponding to a time at which one or more input image elements associated with the subject were collected or a subsequent defined time period, whether the subject had a tumor and/or a stage of progression of the subject's tumor (e.g., along a standard scale and/or by identifying a metric, such total metabolic tumor volume (TMTV)). The received data may further include the pixels of the locations of tumors or tumor cells within the one or more input image elements associated with the subject. Thus, the medical records may include or may be used to identify, with respect to each training/validation input image element 220a-g, one or more labels. The medical records may further indicate each of one or more treatments (e.g., medications) that the subject had been taking and time periods during which the subject was receiving the treatment(s). In some instances, images or scans that are input to one or more classifier subsystems are received from the provider system 255. For example, the provider system 255 may receive images from the imaging device 250 and may then transmit the images or scans (e.g., along with a subject identifier and one or more labels) to the analysis system 205.

In some embodiments, data received at or collected at one or more of the imaging devices 250 may be aggregated with data received at or collected at one or more of the provider systems 255. For example, the analysis system 205 may identify corresponding or identical identifiers of a subject and/or time period so as to associate image data received from the imaging device 250 with label data received from the provider system 255. The analysis system 205 may further use metadata or automated image analysis to process data to determine to which classifier subsystem particular data components are to be fed. For example, image data received from the imaging device 250 may correspond to the whole slide or multiple regions of the slide or tissue. Metadata, automated alignments and/or image processing may indicate, for each image, to which region of the slide or tissue the image corresponds, the type of staining performed, the concentrations of stains used, the lab that performed the staining, a timestamp, the type of scanner used, or any other suitable data as would be understood by one skilled in the art. Automated alignments and/or image processing may include detecting whether an image has image properties corresponding to a slide substrate or a biological structure and/or shape that is associated with a particular cell such as a white blood cell. Label-related data received from the provider system 255 may be slide-specific, region-specific or subject-specific. When label-related data is slide-specific or region specific, metadata or automated analysis (e.g., using natural language processing or text analysis) can be used to identify to which region particular label-related data corresponds. When label-related data is subject-specific, identical label data (for a given subject) may be fed to each classifier subsystem 210a-n during training.

In some embodiments, the computing environment 200 can further include a user device 260, which can be associated with a user that is requesting and/or coordinating performance of one or more iterations (e.g., with each iteration corresponding to one run of the model and/or one production of the model's output(s)) of the analysis system 205. The user may correspond to a physician, investigator (e.g., associated with a clinical trial), subject, medical professional, etc. Thus, it will be appreciated that, in some instances, the provider system 255 may include and/or serve as the user device 260. Each iteration may be associated with a particular subject (e.g., person), who may (but need not) be different than the user. A request for the iteration may include and/or be accompanied with information about the particular subject (e.g., a name or other identifier of the subject, such as a de-identified patient identifier). A request for the iteration may include an identifier of one or more other systems from which to collect data, such as input image data that corresponds to the subject. In some instances, a communication from the user device 260 includes an identifier of each of a set of particular subjects, in correspondence with a request to perform an iteration for each subject represented in the set.

Upon receiving the request, the analysis system 205 can send a request (e.g., that includes an identifier of the subject) for unlabeled input image elements to the one or more corresponding imaging systems 250 and/or provider systems 255. The trained prediction model(s) 215 can then process the unlabeled input image elements to segment non-target or target regions, provide image analysis, provide a diagnosis of disease for treatment or a prognosis for a subject such as a patient, or a combination thereof. A result for each identified subject may include or may be based on the segmenting and/or one or more output metrics from trained prediction model(s) 215 deployed by the classifier subsystems 110a-n. For example, the segmenting and/or one or more output metrics can include or may be based on output generated by the fully connected layer of one or more CNNs. In some instances, such outputs may be further processed using (for example) a softmax function. Further, the outputs and/or further processed outputs may then be aggregated using an aggregation technique (e.g., random forest aggregation) to generate one or more subject-specific metrics. One or more results (e.g., that include plane-specific outputs and/or one or more subject-specific outputs and/or processed versions thereof) may be transmitted to and/or availed to the user device 260. In some instances, some or all of the communications between the analysis system 205 and the user device 260 occurs via a website. It will be appreciated that the CNN system 205 may gate access to results, data and/or processing resources based on an authorization analysis.

While not explicitly shown, it will be appreciated that the computing environment 200 may further include a developer device associated with a developer. Communications from a developer device may indicate what types of input image elements are to be used for each prediction model 215 in the analysis system 205, a number of neural networks to be used, configurations of each neural network including number of hidden layers and hyperparameters, and how data requests are to be formatted and/or which training data is to be used (e.g., and how to gain access to the training data).

Figure 3:
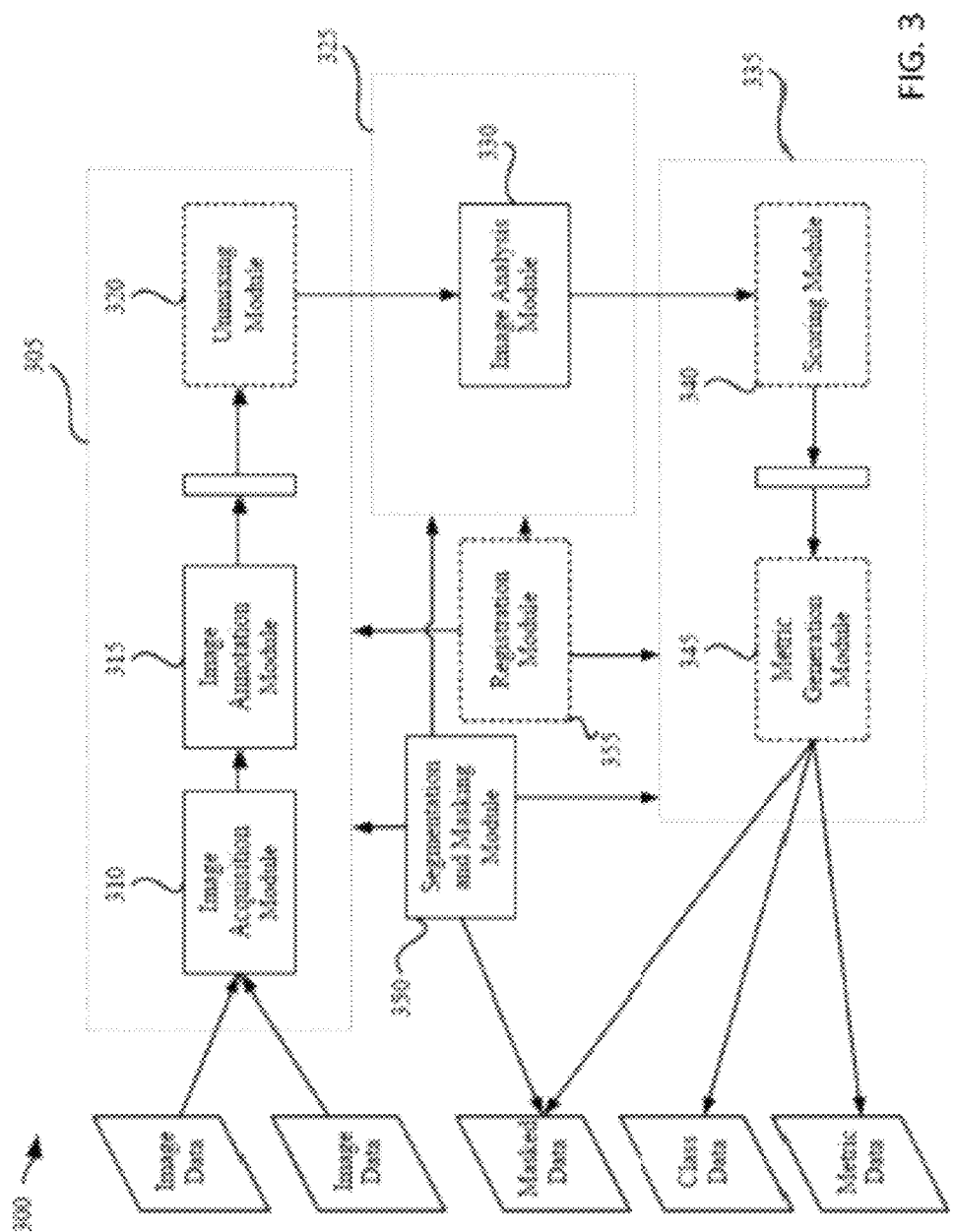
FIG. 3 shows an exemplary schematic diagram 300 representative of a model architecture for non-target region segmentation according to various embodiments.

FIG. 3 illustrates an exemplary schematic diagram 300 representative of a model architecture (e.g., a portion of the analysis system 205 described with respect to FIG. 2) for non-target region segmentation in accordance with various embodiments. The model architecture may comprise a pre-processing stage 305 comprising an image acquisition module 310 to generate or obtain input images including simplex image data (e.g., images where each has a single stain) and/or multiplex image data (e.g., an image having a plurality of stains), an optional image annotation module 315 to electronically annotate a portion of the input images, such as a portion for further analysis, for example, a portion denoting a tumor region or immune cell region, and an optional unmixing module 320 to generate image channel images corresponding to one or more stain channels present in a multiplex image. The model architecture may further comprise a processing stage 325 comprising an image analysis module 330 to detect and/or classify biological material or structures including cells or nuclei (such as tumor cells, stromal cells, lymphocytes, etc.) based on features within the input images (e.g., within an hematoxylin and eosin stain image, a biomarker image, or an unmixed image channel image).

The model architecture may further comprise a post-processing stage 335 comprising an optional scoring module 340 to derive expression predictions and/or scores for each biomarker in each of the identified regions or biological structures, and an optional metric generation module 345 to derive metrics describing the variability between derived expression predictions and/or scores in different regions or biological structures and optionally provide a diagnosis of disease for treatment or a prognosis for a subject such as a patient. The model architecture may further comprise a segmentation and masking module 350 to segment regions or biological structures such as lymphocyte aggregates or clusters of tumor cells in the input images, and generate a mask based on the segmented regions or biological structures, and an optional registration module 355 to map the identified regions or biological structures (e.g. tumor cells or immune cells) from a first image or first set of images within the input images to at least one additional image or a plurality of additional images. The segmentation and masking module 350 and the optional registration module 355 may be implemented within the pre-processing stage 305, the processing stage 325, the post-processing stage 335, or any combination thereof.

In some embodiments, the image acquisition module 310 generates or obtains images or image data of a biological sample having one or more stains (e.g. the images may be simplex images or multiplex images). In some embodiments, the images generated or obtained are RGB images or multispectral images. In some embodiments, the images generated or obtained are stored in a memory device. The images or image data (used interchangeably herein) may be generated or obtained using an imaging device (e.g., the imaging device 250 described with respect to FIG. 2), such as in real-time. In some embodiments, the images are generated or obtained from a microscope or other instrument capable of capturing image data of a specimen-bearing microscope slide, as described herein. In some embodiments, the images are generated or obtained using a 2D scanner, such as one capable of scanning image tiles. Alternatively, the images may be images that have been previously generated (e.g. scanned) and stored in a memory device (or, for that matter, retrieved from a server via a communication network).

In some embodiments, the image acquisition module 310 is used to select a portion of the biological sample for which one or more images or for which image data should be acquired. For example, the image acquisition module 310 may receive an identified region of interest or field of view (FOV). In some embodiments, the region of interest is identified by a user of a system of the present disclosure, or another system communicatively coupled to a system of the present disclosure. Alternatively, and in other embodiments, the image acquisition module 305 retrieves a location or identification of a region or interest from a storage/memory device. In some embodiments, the image acquisition module 310 automatically generates a field of view or a region of interest (ROI), for example, via methods described in PCT/EP2015/062015, the contents of which are incorporated herein in their entirety for all purposes. In some embodiments, the ROI is automatically determined by the image acquisition module 305 based on some predetermined criteria or characteristics that are in or of the image (e.g., for a biological sample stained with more than two stains, identifying an area of the image that comprises just two stains). In some instances, the image acquisition module 310 outputs the ROI.

In some embodiments, the image acquisition module 310 generates or obtains at least two images as input. In some embodiments, the images generated or obtained as input are derived from sequential tissue sections, e.g., sequential sections derived from the same tissue sample. In general, the at least two images received as input each comprise signals corresponding to a stain (including chromogens, fluorophores, quantum dots, etc.). In some embodiments, one of the images has been stained with at least one primary stain (hematoxylin or eosin (H&E)), while another one of the images has been stained in at least one of an IHC assay or an in-situ hybridization (ISH) assay for the identification of a specific biomarker. In some embodiments, one of the images has been stained with both hematoxylin and eosin, while another one of the images has been stained in at least one of an IHC assay or ISH assay for the identification of a specific biomarker. In some embodiments, the input images are multiplex images, e.g., stained for multiple, different markers in a multiplex assay according to methods known to those of ordinary skill in the art.

In some embodiments, the images generated or obtained are optionally annotated by a user (e.g., a medical professional such as a pathologist) to image analysis using an image annotation module 315. In some embodiments, the user identifies portions (e.g. sub-regions) of an image suitable for further analysis. The target regions or non-target regions (e.g., tumorous or immune regions) annotated to generate the slide scores may either be whole tissue regions or a specified set of regions on the digital slide. For example, in some embodiments the identified portions are representative of over-expressive tumorous regions of a specific biomarker, e.g. a specific IHC marker. In other embodiments, a user, medical professional, or pathologist may annotate lymphocyte aggregate regions within the digital slide. In some embodiments, annotated representative fields may be selected by a pathologist to reflect the biomarker expression that the pathologist would use for overall slide interpretation. Annotations may be drawn using an annotation tool provided in a viewer application (e.g., VENTANA VIRTUOSO software) and the annotations may be drawn at any magnification or resolution. Alternatively, or in addition, image analysis operations may be used to automatically detect target regions and non-target regions or other regions using automated image-analysis operations such as segmenting, thresholding, edge detection, etc., and field of views (FOVs—an image portion that has a predetermined size and/or shape) automatically generated based on the detected regions. In some embodiments, the user annotations may be utilized to further train one or more of the models.

In some embodiments, the images generated or obtained may be multiplex images, i.e., the image received is of a biological sample stained with more than one stain. In these embodiments, and prior to further processing, each multiplex image is first unmixed into its constituent channels, such as with an unmixing module 320, where each unmixed channel corresponds to a particular stain or signal. In some embodiments, the unmixed images (often referred to as "channel images" or "image channel images") and may be used as the input for each module described herein. For example, the model architecture may be implemented for assessing inter-marker heterogeneity (an indication of the amount of protein expression heterogeneity of a biomarker in a sample) determined with a first H&E image, a second multiplex image stained for a plurality of cluster of differentiation markers (CD3, CD8, etc.), and a plurality of simplex images each stained for a particular biomarker (e.g., ER, PR, Ki67, etc.). In this example, the multiplex image is first unmixed into its constituent channel images, and those channel images may be used along with the H&E image and the plurality of simplex images to determine inter-marker heterogeneity.

Following image acquisition and/or unmixing, input images or unmixed image channel images are processed with an image analysis algorithm provided by the image analysis module 330 to identify and classify cells and/or nuclei. The procedures and algorithms described herein may be adapted to identify and classify various types of cells or cell nuclei based on features within the input images, including identifying and classifying tumor cells, non-tumor cells, stroma cells, lymphocytes, non-target stain, etc. One of ordinary skill in the art should appreciate that the nucleus, cytoplasm and membrane of a cell have different characteristics and that differently stained tissue samples may reveal different biological features. Specifically, one of ordinary skill in the art should appreciate that certain cell surface receptors can have staining patterns localized to the membrane, or localized to the cytoplasm. Thus, a "membrane" staining pattern is analytically distinct from a "cytoplasmic" staining pattern. Likewise, a "cytoplasmic" staining pattern and a "nuclear" staining pattern are analytically distinct. Each of these distinct staining patterns may be used as features for identifying cells and/or nuclei. For example, stromal cells may be strongly stained by FAP, whereas tumor epithelial cells may be strongly stained by EpCAM, while cytokeratins may be stained by panCK. Thus, by utilizing different stains different cell types may be differentiated and distinguished during image analysis to provide a classification solution.

Methods of identifying, classifying, and/or scoring nuclei, cell membranes, and cell cytoplasm in images of biological samples having one or more stains are described in U.S. Pat. No. 7,760,927 ("the '927 Patent"), the contents of which are incorporated herein in their entirety for all purposes. For example, the '927 Patent describes an automated method for simultaneously identifying a plurality of pixels in an input image of a biological tissue stained with a biomarker, including considering a first color plane of a plurality of pixels in a foreground of the input image for simultaneous identification of cell cytoplasm and cell membrane pixels, wherein the input image has been processed to remove background portions of the input image and to remove counterstained components of the input image; determining a threshold level between cell cytoplasm and cell membrane pixels in the foreground of the digital image; and determining simultaneously with a selected pixel and its eight neighbors from the foreground if the selected pixel is cell cytoplasm pixel, a cell membrane pixel or a transitional pixel in the digital image using the determined threshold level. In some embodiments, tumor nuclei are automatically identified by first identifying candidate nuclei and then automatically distinguishing between tumor nuclei and non-tumor nuclei. Numerous methods of identifying candidate nuclei in images of tissue are known in the art. For example, automatic candidate nucleus detection can be performed by applying a radial-symmetry-base method, a radial-symmetry-based method of Parvin such as on the Hematoxylin image channel or a biomarker image channel after unmixing (see Parvin, Bahram, et al. "Iterative voting for inference of structural saliency and characterization of subcellular events." Image Processing, IEEE Transactions on 16.3 (2007): 615-623, the contents of which are incorporated herein in their entirety for all purposes).

For example, in some embodiments the images obtained as input are processed such as to detect nucleus centers (seeds) and/or to segment the nuclei. For example, instructions may be provided and executed to detect nucleus centers based on radial-symmetry voting using the techniques of Parvin (noted above). In some embodiments, nuclei are detected using radial symmetry to detect centers of nuclei and then the nuclei are classified based on the intensity of stains around the cell centers. In some embodiments, a radial symmetry based nuclei detection operation is used as described in commonly-assigned and co-pending patent application WO2014140085A1, the contents of which are incorporated herein in their entirety for all purposes. For example, an image magnitude may be computed within an image and one or more votes at each pixel are accumulated by adding the summation of the magnitude within a selected region. Mean shift clustering may be used to find the local centers in the region, with the local centers representing actual nuclear locations. Nuclei detection based on radial symmetry voting is executed on color image intensity data and makes explicit use of the a priori domain knowledge that the nuclei are elliptical shaped blobs with varying sizes and eccentricities. To accomplish this, along with color intensities in the input image, image gradient information is also used in radial symmetry voting and combined with an adaptive segmentation process to precisely detect and localize the cell nuclei. A "gradient" as used herein is, for example, the intensity gradient of pixels calculated for a particular pixel by taking into consideration an intensity value gradient of a set of pixels surrounding said particular pixel. Each gradient may have a particular "orientation" relative to a coordinate system whose x- and y-axis are defined by two orthogonal edges of the digital image. For instance, nuclei seed detection involves defining a seed as a point which is assumed to lie inside a cell nucleus and serve as the starting point for localizing the cell nuclei. The first step is to detect seed points associated with each cell nuclei using a highly robust approach based on the radial symmetry to detect elliptical shaped blobs, structures resembling cell nuclei. The radial symmetry approach operates on the gradient image using a kernel based voting procedure. A voting response matrix is created by processing each pixel that accumulates a vote through a voting kernel. The kernel is based on the gradient direction computed at that particular pixel and an expected range of minimum and maximum nucleus size and a voting kernel angle (typically in the range [p/4, p/8]). In the resulting voting space, local maxima locations that have a vote value higher than a predefined threshold value are saved out as seed points. Extraneous seeds may be discarded later during subsequent segmentation or classification processes. Other methods are discussed in U.S. Patent Publication No. 2017/0140246, the disclosure of which is incorporated by reference herein.

After candidate nuclei are identified, the candidate nuclei may be further analyzed to distinguish tumor nuclei from other candidate nuclei. The other candidate nuclei may be further classified (for example, by identifying lymphocyte nuclei and stroma nuclei). In some embodiments, a learnt supervised classifier is applied to identify tumor nuclei, as described further herein. For example, the learnt supervised classifier is trained on nuclei features to identify tumor nuclei and then applied to classify the nucleus candidate in the test image as either a tumor nucleus or a non-tumor nucleus. Optionally, the learnt supervised classifier may be further trained to distinguish between different classes of non-tumor nuclei, such as lymphocyte nuclei and stromal nuclei. In some embodiments, the learnt supervised classifier used to identify tumor nuclei is a random forest classifier. For example, the random forest classifier may be trained by: (i) creating a training set of tumor and non-tumor nuclei, (ii) extracting features for each nucleus, and (iii) training the random forest classifier to distinguish between tumor nuclei and non-tumor nuclei based on the extracted features. The trained random forest classifier may then be applied to classify the nuclei in a test image into tumor nuclei and non-tumor nuclei. Optionally, the random forest classifier may be further trained to distinguish between different classes of non-tumor nuclei, such as lymphocyte nuclei and stromal nuclei.

Nuclei may be identified using other techniques known to those of ordinary skill in the art. For example, an image magnitude may be computed from a particular image channel of one of the FI&E or IHC images, and each pixel around a specified magnitude may be assigned a number of votes that is based on a summation of the magnitude within a region around the pixel. Alternatively, a mean shift clustering operation may be performed to find the local centers within a voting image, which represents the actual location of the nucleus. In other embodiments, nuclear segmentation may be used to segment the entire nucleus based on the now-known centers of the nuclei via morphological operations and local thresholding. In yet other embodiments, model based segmentation may be utilized to detect nuclei (i.e. learning the shape model of the nuclei from a training data set and using that as the prior knowledge to segment the nuclei in the testing image).

In some embodiments, the nuclei are then subsequently segmented using thresholds individually computed for each nucleus. For example, Otsu's method maybe used for segmentation in a region around an identified nucleus since it is believed that the pixel intensity in the nuclear regions varies. As will be appreciated by those of ordinary skill in the art, Otsu's method is used to determine an optimal threshold by minimizing the intra-class variance and is known to those of skill in the art. More specifically, Otsu's method is used to automatically perform clustering-based image thresholding or, the reduction of a gray level image to a binary image. The algorithm assumes that the image contains two classes of pixels following a bi-modal histogram (foreground pixels and background pixels). It then calculates the optimum threshold separating the two classes such that their combined spread (intra-class variance) is minimal, or equivalent (because the sum of pairwise squared distances is constant), so that their inter-class variance is maximal.

In some embodiments, the systems and methods further comprise automatically analyzing spectral and/or shape features of the identified nuclei in an image for identifying nuclei of non-tumor cells. For example, blobs may be identified in the first digital image in a first step. A "blob" as used herein can be, for example, a region of a digital image in which some properties, e.g. the intensity or grey value, are constant or vary within a prescribed range of values. All pixels in a blob can be considered in some sense to be similar to each other. For example, blobs may be identified using differential methods which are based on derivatives of a function of position on the digital image, and methods based on local extrema. A nuclear blob is a blob whose pixels and/or whose outline shape indicate that the blob was probably generated by a nucleus stained with the first stain. For example, the radial symmetry of a blob could be evaluated to determine if the blob should be identified as a nuclear blob or as any other structure, e.g. a staining artifact. For example, in case a blob has a lengthy shape and is not radially symmetric, said blob may not be identified as a nuclear blob but rather as a staining artifact. Depending on the embodiment, a blob identified to be a "nuclear blob" may represent a set of pixels which are identified as candidate nuclei and which may be further analyzed for determining if said nuclear blob represents a nucleus. In some embodiments, any kind of nuclear blob is directly used as an "identified nucleus." In some embodiments, filtering operations are applied on the identified nuclei or nuclear blobs for identifying nuclei which do not belong to biomarker-positive tumor cells and for removing said identified non-tumor nuclei from the list of already identified nuclei or not adding said nuclei to the list of identified nuclei from the beginning. For example, additional spectral and/or shape features of the identified nuclear blob may be analyzed to determine if the nucleus or nuclei ear blob is a nucleus of a tumor cell or not. For example, the nucleus of a lymphocyte is larger than the nucleus of other tissue cell, e.g. of a lung cell. In case the tumor cells are derived from a lung tissue, nuclei of lymphocytes are identified by identifying all nuclear blobs of a minimum size or diameter which is significantly larger than the average size or diameter of a normal lung cell nucleus. The identified nuclear blobs relating to the nuclei of lymphocytes may be removed (i.e., "filtered out from") the set of already identified nuclei. By filtering out the nuclei of non-tumor cells, the accuracy of the method may be increased. Depending on the biomarker, also non-tumor cells may express the biomarker to a certain extent, and may therefore produce an intensity signal in the first digital image which does not stem from a tumor cell. By identifying and filtering out nuclei which do not belong to tumor cells from the totality of the already identified nuclei, the accuracy of identifying biomarker-positive tumor cells may be increased. These and other methods are described in US Patent Publication 2017/0103521, the contents of which are incorporated herein in their entirety for all purposes. In some embodiments, once the seeds are detected, a locally adaptive thresholding method may be used, and blobs around the detected centers are created. In some embodiments, other methods may also be incorporated, such as marker based watershed algorithms can also be used to identify the nuclei blobs around the detected nuclei centers. These and other methods are described in PCT/EP2016/051906, published as WO2016/120442, the contents of which are incorporated herein in their entirety for all purposes.

In some embodiments, a variety of marker expression scores are calculated for each stain or biomarker within each cell cluster within each image (simplex images or unmixed image channel images from a multiplex image) using the scoring module 340. The scoring module 340, in some embodiments, utilizes data acquired during the detection and classification of cells by the image analysis module 330. For example, the image analysis module 330 may comprise a series of image analysis algorithms and may be used to determine a presence of one or more of a nucleus, a cell wall, a tumor cell, or other structures within the identified cell clusters, as described herein. In some embodiments, derived stain intensity values and counts of specific nuclei for each field of view may be used by the scoring module 340 to determine various marker expression scores, such as percent positivity or an H-Score. Methods for scoring are described in further detail in commonly-assigned and co-pending applications WO/2014/102130A1 "Image analysis for breast cancer prognosis" filed Dec. 19, 2013, and WO/2014/140085A1 "Tissue object-based machine learning system for automated scoring of digital whole slides", filed Mar. 12, 2104, the contents of each are hereby incorporated by reference in their entirety herein. For example, automated image analysis algorithms in the image analysis module 330 may be used to interpret each one of the IFIC slides in the series to detect tumor nuclei that are positively and negatively stained for a particular biomarker, such as Ki67, ER, PR, FIER2, etc. Based on the detected positive and negative tumor nuclei, various slide level scores such as marker percent positivity, H-scores, etc. may be computed using the scoring module 340.

In some embodiments, the expression score is an H-score is used to assess the percentage of tumor cells with cell membrane staining graded as 'weak,' moderate' or 'strong.' The grades are summated to give an overall maximum score of 300 and a cut-off point of 100 to distinguish between a 'positive' and 'negative'. For example, a membrane staining intensity (0, 1+, 2+, or 3+) is determined for each cell in a fixed field of view (or here, each cell in a tumor or cell cluster). The H-score may simply be based on a predominant staining intensity, or more complexly, can include the sum of individual H-scores for each intensity level seen. In other embodiments, the expression score is an Allred score. The Allred score is a scoring system which looks at the percentage of cells that test positive for hormone receptors, along with how well the receptors show up after staining (this is called "intensity"). In other embodiments, the expression score is percent positivity. In the context of scoring a breast cancer sample stained for the PR and Ki-67 biomarkers, for the PR and Ki-67 slides, the percent positivity is calculated (e.g., the total number of nuclei of cells (e.g., malignant cells) that are stained positive in each field of view in the digital image of a slide are summed and divided by the total number of positively and negatively stained nuclei from each of the fields of view of a digital image) in a single slide as follows: Percent positivity=number of positively stained cells/(number of positively stained cells+number of negatively stained cells). In other embodiments, the expression score is an IHC combination score, which is a prognostic score based on a number of IHC markers, where the number of markers is greater than one. IHC4 is one such score based on four measured IHC markers, namely ER, HER2, Ki-67, and PR in a breast cancer sample (for example see Cuzick et al., J. Clin. Oncol. 29:4273-8, 2011, and Barton et al., Br. J. Cancer 1-6, Apr. 24, 2012, both herein incorporated by reference).

Following image analysis and determination of expression scores for each marker in each identified cluster or mapped cluster, metrics may be derived from various identified clusters and biological structures using the metric generation module 345. In some instances, a morphology metric may be computed by applying various image analysis algorithms on pixels contained in or surrounding a nuclear blob or seed. In some embodiments, the morphology metric includes area, minor, and major axis lengths, perimeter, radius, solidity, etc. At the cellular level, such metrics may be used to classify a nucleus as belonging to a healthy or diseased cell. At the tissue level, the statistics of these features over the tissue are exploited in the classification of a tissue as diseased or not. In some instances, an appearance metric may be computed for a particular nucleus by comparing pixel intensity values of pixels contained in or surrounding a nuclear blob or seed used for identifying the nucleus, whereby the compared pixel intensities are derived from different image channels (e.g. a background channel, a channel for the staining of a biomarker, etc.). In some embodiments, the metrics derived from appearance features are computed from percentile values (e.g. the 10th, 50th, and 95th percentile values) of pixel intensities and of gradient magnitudes computed from different image channels. For example, at first, a number P of X-percentile values (X=10, 50, 95) of pixel values of each of a plurality IC of image channels (e.g. three channels: HTX, DAB, luminance) within a nuclear blob representing the nucleus of interest are identified. Computing appearance feature metrics may be advantageous since the derived metrics may describe the properties of the nuclear regions as well as describe the membrane region around the nuclei.

In some instances, a background metric may be computed that is indicative of the appearance and/or stain presence in cytoplasm and cell membrane features of the cell comprising the nucleus for which a background feature was extracted from the image. A background feature and a corresponding metrics can be computed for a nucleus and a corresponding cell depicted in a digital image e.g. by identifying a nuclear blob or seed representing the nucleus; analyzing a pixel area (e.g. a ribbon of 20 pixels—about 9 microns—thickness around the nuclear blob boundary) directly adjacent to the identified set of cells are computed in, therefore capturing appearance and stain presence in cytoplasm and membrane of the cell with this nucleus together with areas directly adjacent to the cell. In some instances, a color metric may be derived from color that includes color ratios, R/(R+G+B) or color principal components. In other embodiments, a color metric derived from color includes local statistics of each of the colors (mean/median/variance/std dev) and/or color intensity correlations in a local image window. In some instances, an intensity metric may be derived from groups of adjacent cells with certain specific property values that set up between the dark and the white shades of grey colored cells represented in an image. The correlation of the color feature may define an instance of the size class, thus this way the intensity of these colored cells determines the affected cell from its surrounding cluster of dark cells.

In some instances, other features may be considered and used as the basis for computation of metrics such as texture features or spatial features. By way of another example, the expression scoring may be utilized as a predictive measure or to guide treatment. For example, and in the context of breast cancer and the ER and PR biomarkers, a sample that tests positive may guide the decision to provide hormonal therapy during the course of treatment. The skilled artisan will also appreciate that not all clusters within a biological sample may have the same score for any particular marker. By being able to determine a heterogeneity score or metric describing the variability between clusters, additional guidance may be provided to make an informed treatment decision. In some embodiments, heterogeneity is determined to measure how different clusters compare to each other. Heterogeneity can be measured by a variability metric describing how, for example, different the protein expression levels among the various identified and mapped clusters compared with each other, as described in WO2019110567A1, the contents of which are incorporated herein in their entirety for all purposes. In some embodiments, heterogeneity is measured between all clusters identified. In other embodiments, heterogeneity is measured between only a subset of identified clusters (e.g. clusters meeting certain predetermined criteria).

In some embodiments, the images received as input may be segmented and masked by the segmentation and masking module 350. For example, a trained convolutional neural network architecture or model may be used to segment non-target regions and/or target regions, which can then be masked for analysis before, during, or after inputting images to an image analysis algorithm. In some embodiments, the input images are masked such that only tissue regions are present in the images. In some embodiments, a tissue region mask is generated to mask non-tissue regions from tissue regions. In some embodiments, a tissue region mask may be created by identifying the tissue regions and excluding the background regions (e.g. regions of a whole slide image corresponding to glass with no sample, such as where there exists only white light from the imaging source).

In some embodiments, a segmentation technique is used to generate tissue region masked images by masking tissue regions from non-tissue regions in the input images. In some embodiments, an image segmentation technique is utilized to distinguish between the digitized tissue data and the slide in the image, the tissue corresponding to the foreground and the slide corresponding to the background. In some embodiments, the segmentation and masking module 350 computes the Area of Interest (AOI) in a whole slide image in order to detect all tissue regions in the AOI while limiting the amount of background non-tissue area that is analyzed. A wide range of image segmentation techniques (e.g., HSV color-based image segmentation, Lab image segmentation, mean-shift color image segmentation, region growing, level set methods, fast marching methods, etc.) can be used to determine, for example, boundaries of the tissue data and non-tissue or background data. Based at least in part on the segmentation, the segmentation and masking module 350 can generate a tissue foreground mask that can be used to identify those portions of the digitized slide data that correspond to the tissue data. Alternatively, the component can generate a background mask used to identify those portions of the digitized slide date that do not correspond to the tissue data.

This identification may be enabled by image analysis operations such as edge detection, etc. A tissue region mask may be used to remove the non-tissue background noise in the image, for example the non-tissue regions. In some embodiments, the generation of the tissue region mask comprises one or more of the following operations (but not limited to the following operations): computing the luminance of the low resolution input image, producing a luminance image, applying a standard deviation filter to the luminance image, producing a filtered luminance image, and applying a threshold to filtered luminance image, such that pixels with a luminance above a given threshold are set to one, and pixels below the threshold are set to zero, producing the tissue region mask. Additional information and examples relating to the generation of tissue region masks is disclosed in PCT/EP/2015/062015, entitled "An Image Processing Method and System for Analyzing a Multi-Channel Image Obtained from a Biological Tissue Sample Being Stained by Multiple Stains," the contents of which are incorporated herein in their entirety for all purposes.

In addition to masking non-tissue regions from tissue regions, the segmentation and masking module 350 may also mask other areas of interest as needed, such as a portion of a tissue identified as belonging to a non-target region or a certain tissue type (e.g., lymphoid aggregate regions) or a portion of a tissue identified as belonging to a target region or a certain tissue type (e.g., a suspected tumor region). In various embodiments, non-target region segmentation such as lymphocyte aggregate region segmentation is performed by a CNN model (e.g., a CNN model associated with classifier subsystem 210a as described with respect to FIG. 2). In some embodiments, the CNN model is a two-dimensional segmentation model. For example, the CNN model may be a U-Net with residual blocks, dilation, and depth-wise convolutions. The pre-processed or processed image data (e.g., two-dimensional regional or whole slide images) may be used as input into the U-Net. The U-Net comprises a contracting path supplemented with an expansive path, where the pooling operations of successive layers in the expansive path are replaced with upsampling operators. Thus, these successive layers increase the resolution of the output. Based at least in part on the segmentation, the U-Net can generate a non-target region foreground mask that can be used to identify those portions of the digitized slide data that correspond to the non-target region data. Alternatively, the component can generate a background mask used to identify those portions of the digitized slide data that do not correspond to the non-target region data. The outputs of the U-Net may be the foreground non-target region mask representing the locations of non-target regions present in the underlying images or the background non-target region mask representing those portions of the digitized slide data that do not correspond to the non-target region data (e.g., target regions).

In some embodiments, biological material or structures such as tumor cells or cell clusters identified in one or more images are mapped to one or more additional images using the registration module 355 and a registration process. Registration is the process of transforming different sets of data, here images, or cell cluster within images, into one coordinate system. More specifically, registration is the process of aligning two or more images and, in general, involves designating one image as the reference (also called the reference image or the fixed image), and applying geometric transformations to the other images so that they align with the reference. A geometric transformation maps locations in one image to new locations in another image. The step of determining the correct geometric transformation parameters is key to the image registration process. In some embodiments, the image registration is performed using the methods described in WO/2015/049233, entitled "Line-Based Image Registration and Cross-Image Annotation Devices, Systems and Methods," filed on Sep. 30, 2014, the contents of which are incorporated herein in their entirety for all purposes. WO/2015/049233 describes a registration process comprising a coarse registration process used alone or in combination with a fine registration process. In some embodiments, the coarse registration process may involve selecting digital images for alignment, generating a foreground image mask from each of the selected digital images, and matching tissue structure between the resultant foreground images. In further embodiments, generating a foreground image mask involves generating a soft-weighted foreground image from the whole slide image of a stained tissue section and applying OTSU thresholding to the soft-weighted foreground image to produce a binary soft-weighted image mask. In other further embodiments, generating a foreground image mask involves generating a binary soft-weighted image mask from a whole slide image of a stained tissue section, separately generating a gradient magnitude image mask from the same whole slide image, applying OTSU thresholding to the gradient image mask to produce a binary gradient magnitude image mask, and combining the binary soft-weighted image and the binary gradient magnitude image mask using a binary OR operation to generate the foreground image mask. A "gradient" as used herein is, for example, the intensity gradient of pixels calculated for a particular pixel by taking into consideration an intensity value gradient of a set of pixels surrounding said particular pixel. Each gradient may have a particular "orientation" relative to a coordinate system whose x- and y-axis are defined by two orthogonal edges of the digital image. A "gradient orientation feature" may be a data value that indicates the orientation of the gradient within said coordinate system.

In some embodiments, matching tissue structure involves computing line-based features from the boundary of each of the resultant foreground image masks, computing global transformation parameters between a first set of line-features on a first foreground image mask and a second set of line-features on a second foreground image mask, and globally aligning the first and second image based on the transformation parameters. In yet further embodiments, the coarse registration process includes mapping the selected digital images based on the global transformation parameters to a common grid, which grid may encompass the selected digital images. In some embodiments, the fine registration process may involve identifying a first sub-region of a first digital image in the set of aligned digital images; identifying a second sub-region on a second digital image in the set of aligned digital images, where the second sub-region is larger than the first sub-region and the first sub-region is located substantially within the second sub-region on common grid; and, computing an optimized location for the first sub-region in the second sub-region.

Figure 4:
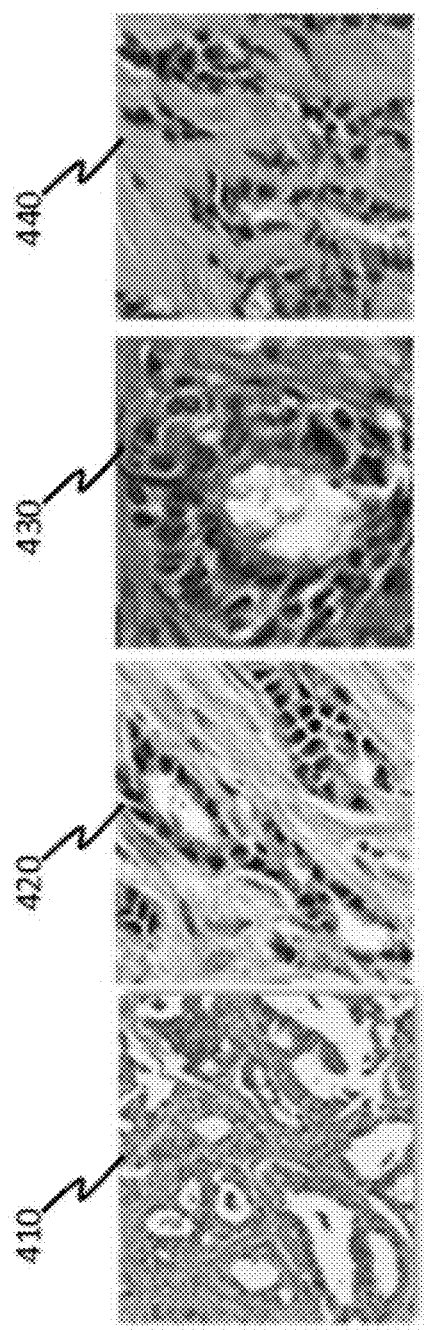
FIG. 4 depicts examples of stain variations across different H&E slide images according to various embodiments.

FIG. 4 depicts examples of stain variations across different H&E slide images 410, 420, 430, 440. In various instances, H&E slides may vary in color and brightness. For example, different pathology laboratories and/or pathologists may elect to stain a tissue sample based on individual preferences, different staining processes, and/or different staining/scanning equipment. Furthermore, the H&E slide images may be of different types of tissue (e.g., tumor, stroma and necrosis) and/or from different organs (e.g., liver, prostate, breast, etc.). Thus, the global model(s) 112, 114 should be trained appropriately so that the model is generic enough to still operate accurately despite the variations in color, tissue, and organs, or multiple models may be utilized.

Figure 5:
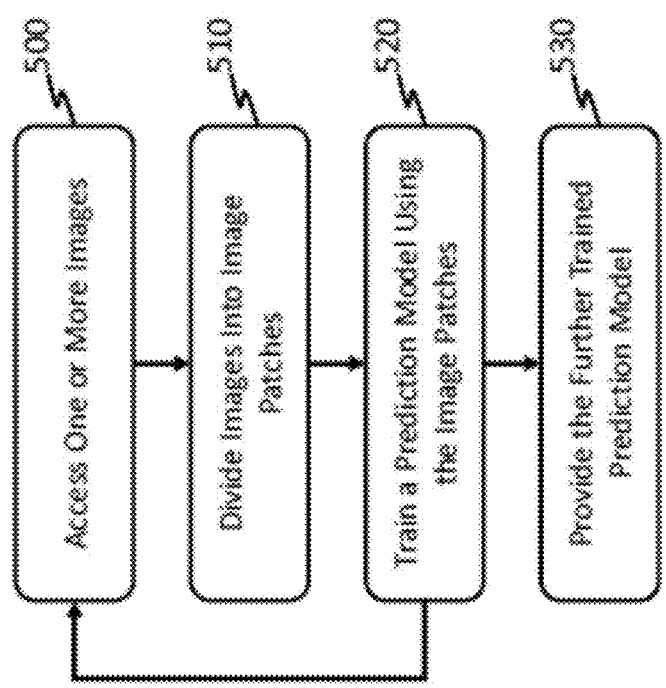
FIG. 5 shows a process for training a prediction model in accordance with various embodiments.

FIG. 5 shows a process for training a prediction model in accordance with various embodiments.

The process for training begins at block 500, at which a plurality tile images for a specimen are accessed. One or more tile images of the plurality tile images comprise annotations (e.g., to identify regions having tumor cells, to segment non-target regions and target regions, or any other suitable annotation) of the one or more tile images. At block 510, the one or more tile images may be split into image patches (e.g., of a size of 256 pixels×256 pixels). At block 520, a prediction model such as a two-dimensional segmentation model is trained using the one or more tile images or the image patches. In some instances, the two-dimensional segmentation model is a modified U-Net model comprising contracting path and an expansive path, each of the contracting path and the expansive path having a maximum of 256 channels, and one or more layers of the contracting path implement spatial drop out. The training may comprise performing iterative operations to find a set of parameters for the predictive model that minimizes a loss function for the predictive model. Each iteration may involve finding the set of parameters for the prediction model so that a value of the loss function using the set of parameters is smaller than a value of the loss function using another set of parameters in a previous iteration. The loss function is constructed to measure a difference between outputs predicted using the prediction model and the annotations contained in the one or more tile images or image patches. In some instances, the training further comprises adjusting a learning rate of the modified U-Net by reducing the learning rate according to a predefined schedule. The predefined schedule may be a step decay schedule that drops the learning rate by a predetermined factor every predetermined number of epochs for optimizing the loss function. In certain instances, the loss function is a binary cross entropy loss function. At block 530, the further trained prediction model may be provided to the central server after a number of iterations, length of time, or after the model has been modified more than a threshold amount. For example, the further trained prediction model may be deployed for execution in a FL image analysis environment, as described with respect to FIGS. 2 and 3.

Figure 6:
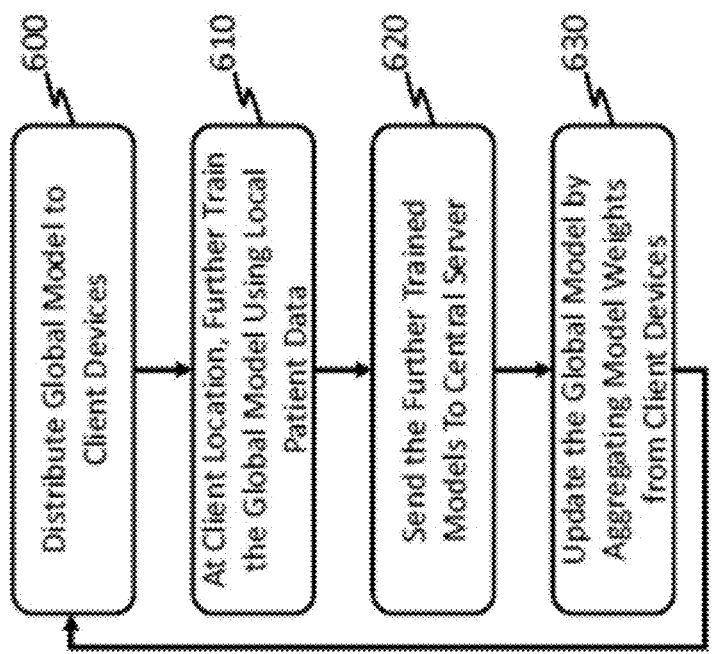
FIG. 6 shows a process for a round of FL training of prediction models in accordance with various embodiments.

FIG. 6 shows a process for a round of FL training of prediction models in accordance with various embodiments.

The FL process for a round of training begins at block 600, at which each of the client devices is provided with one or more global models for use in classification. Each of the client devices may have access to local data that may be used for further training of the provided global model(s). One or more tile images from the local data include annotations (e.g., to identify regions having tumor cells, to segment non-target regions and target regions, or any other suitable annotation) of the one or more tile images. As described above, the one or more tile images may be split into image patches. At block 610, the prediction model (e.g., the global model) is further trained on the one or more tile images or the image patches. At block 620, the further trained prediction model is provided to the central server after the local training data has been exhausted. At block 630, the server may receive one or more further trained models and aggregate the weights from those models into the global model. The weights may be aggregated by performing an average, weighted average, or other appropriate method for combining the weights as would be understood by those skilled in the art. For example, in some embodiments, the weights may be incorporated into the global model based on a weighted average that is based on the number of training rounds (e.g., slides analyzed) performed.

Figure 7:
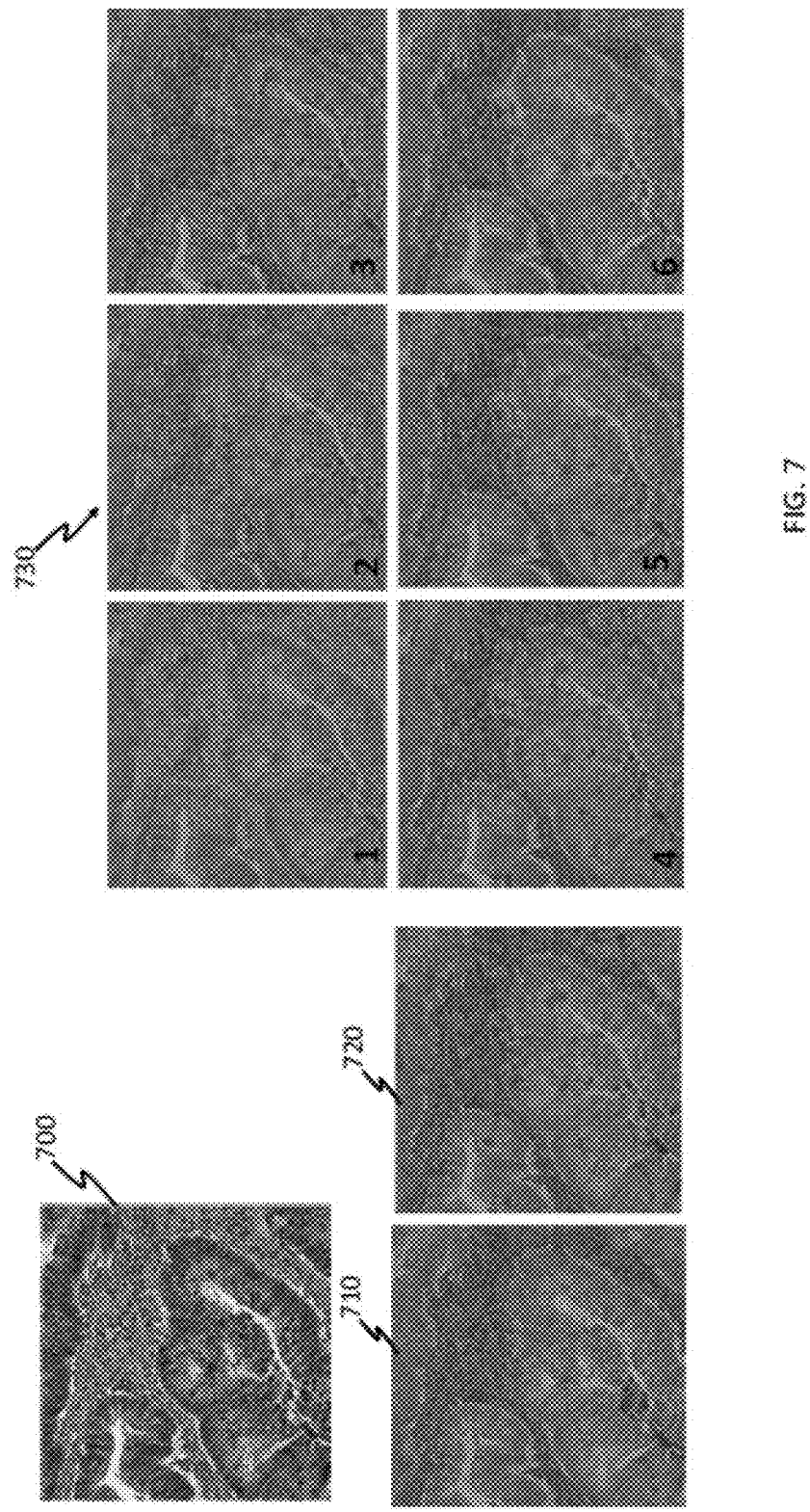
FIG. 7 shows results produced after multiple rounds of FL training of prediction models in accordance with various embodiments.

FIG. 7 shows results produced after multiple rounds of FL training of prediction models in accordance with various embodiments.

The improved accuracy provided by multiple training rounds may be visualized. For example, an H&E image 700 may be used to validate the training of the FL system. A groundtruth 710 may be provided to compare to the output of the model. In this example, the image is colored blue to indicate a tumor and purple for all other tissue. An example result 720 using a model trained using centralized data is also provided. In this example, six rounds of classification and training are performed and the resulting classification 730 produced by each round is depicted. After each round of FL, the global model is further trained at one or more client systems and the results converge towards the groundtruth 710.

FIG. 8 shows a process for a round of FL training of prediction models in accordance with various embodiments.

In various embodiments, the FL process for a round of training begins at block 800, at which each of the client devices is provided with one or more global models for use in classification. As described above, each of the client devices may have access to local data that may be used for further training of the provided global model(s) and one or more tile images from the local data include annotations (e.g., to identify regions having tumor cells, to segment non-target regions and target regions, or any other suitable annotation). Furthermore, the local data may also include metadata that further describe the local data. For example, the metadata may include information regarding how the sample was prepared (e.g., stains applied, stain concentrations, and/or any other relevant information related to sample preparation), equipment used (e.g., staining equipment, scanning equipment, etc.), and further patient information. At block 810, the metadata may be elevated to determine if any data compensation or normalization needs to be administered. For example, certain scanning devices may introduce artifacts that require compensation. In another example, some staining concentrations may yield excessively light or dark coloration that can be compensated for. Thus, at block 820, the system may compensate for a data imbalance using the metadata or other information. At block 830, the model is further trained on the one or more tile images or the image patches, the updated model is provided to the centralized server, and the global model is updated. At block 840, the updated global model is tested using a validation dataset to confirm an improvement in the model. When the global model is improved, the changes may be saved. At block 850, the server may distributed the updated model to each of the client devices.

FIG. 9 shows a process for a receiving an updated model from a client in accordance with various embodiments.

In various embodiments, the centralized server receives an updated model and metadata from a client device. As described above, at block 910 the system may evaluate in the metadata associated with the local training data. In various embodiments, the system may be configured to have multiple global classifiers that are selected according to various metadata. For example, the separate classifiers may be used for locations utilizing certain equipment or staining techniques. Thus, at block 920, the system may be configured to determine if the updated classifier should be used to update one of a plurality of global models or if a new global model should be added. At block 930, the received updated model is normalized and used to update one of the global models. At block 940, the newly updated model is verified using the validation dataset. At block 950, it has been determined that a new global model should be added. Thus, the received updated model is verified. At block 960, the verified model is then added to the plurality of global models. At block 970, the updated model is distributed to the appropriate client devices.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A computer-implement method for using a federated learning classifier comprising:
   distributing, by a centralized server located at a first location to a plurality of client devices that are located at client locations, a global model configured to classify one or more cell types or one or more tissue types and/or segment the one or more cell types or the one or more tissue types within digital pathology images, wherein:
      the digital pathology images depict at least a portion of slides of a tissue of the one or more tissue types, and
      the slides have been prepared using colored stains that bind to select components of the tissue;
   receiving, by the centralized server an updated model and metadata associated with a plurality of slide images from at least one of the plurality of client devices, wherein the updated model has been further trained at the at least one of the plurality of client devices using the plurality of slide images and a plurality of corresponding annotations, wherein the metadata comprises an identification of at least one of a region of a slide or the tissue corresponding to each image of the plurality of slide images, a type of staining performed, a concentration of a stain, and an equipment used in staining or scanning;
   aggregating, by the centralized server, the updated model with the global model to generate an updated global model based on the metadata; and
   distributing the updated global model to at least one of the plurality of client devices.

2. The computer-implemented method of claim 1, wherein aggregating the updated model with the global model to generate an updated global model comprises performing an averaging of a least one weight of the global model with at least on weight of the updated model.

3. The computer-implemented method of claim 2, wherein performing the averaging comprises performing a weighted average according of the at least one weight of the updated model with the at least one weight of the global model according to number of the plurality of slide images used to further train the updated model and a total number of images used to train the global model.

4. The computer-implemented method of claim 1, wherein the annotations are provided by a user observing an output of the global model on a slide image and the annotations comprise a modification to the output produced by the global model.

5. The computer-implemented method of claim 1, further comprising receiving, by the centralized server, metadata associated with the plurality of slide images, wherein aggregating further comprises normalizing the further trained model according to the metadata.

6. The computer-implemented method of claim 1, further comprising verifying, by the centralized server, a performance improvement of the updated global model relative to the global model using a validation dataset.

7. A computer-implement method for using a federated learning classifier in digital pathology comprising:
   distributing, by a centralized server located at a first location, a global model configured to classify one or more cell types or one or more tissue types and/or segment the one or more cell types or the one or more tissue types within digital pathology images to a plurality of client devices located at client locations, wherein:
      the digital pathology images depict at least a portion of slides of a tissue of the one or more tissue types, and
      the slides have been prepared using colored stains that bind to select components of the tissue;
   training, by a client device from the plurality of client devices, the global model using a plurality of images of a specimen to generate at least one further trained model, wherein one or more images of the plurality of images comprise at least one annotation;
   providing, by the client device, the further trained model and metadata associated with the plurality of images to the centralized server, wherein the metadata comprises an identification of at least one of a region of a slide or the tissue corresponding to each image of the plurality of images, a type of staining performed, a concentration of a stain, and an equipment used in staining or scanning;
   aggregating, by the centralized server, the further trained model with the global model to generate an updated global model; and
   distributing the updated global model to the plurality of client devices.

8. The computer-implemented method of claim 7, further comprising:
   generating, by the client device, metadata relevant to the plurality of images; and
   providing, by the client device, the metadata to the centralized server, wherein aggregating, by the centralized server, the further trained model with the global model to generate an updated global model further comprises normalizing the further trained model according to the metadata.

9. The computer-implemented method of claim 8, wherein the metadata comprises at least one of a region of a slide or tissue that the image corresponds, a type of staining performed, a concentration of a stain, and an equipment used in staining or scanning.

10. The computer-implemented method of claim 7, further comprising verifying, by the centralized server, a performance of the updated global model relative to the global model using a validation dataset.

11. The computer-implemented method of claim 10, further comprising rolling back the update to the global model when the performance of the updated global model is inferior to the global model.

12. The computer-implemented method of claim 7, wherein aggregating the updated model with the global model to generate an updated global model comprises performing an averaging of a least one weight of the global model with at least one weight of the updated model.

13. The computer-implemented method of claim 12, wherein performing the averaging comprises performing a weighted average according of the at least one weight of the updated model with the at least one weight of the global model according to number of the plurality of images used to further train the updated model and a total number of images used to train the global model.

14. The computer-implemented method of claim 8, wherein sending the updated model is performed after a threshold a number of iterations, length of time, or after the model has been modified more than a threshold amount.

* * * * *